United States Patent [19]

Yukl

[11] Patent Number: 5,083,089
[45] Date of Patent: Jan. 21, 1992

[54] FLUID MIXTURE RATIO MONITORING METHOD AND APPARATUS

[75] Inventor: Tex Yukl, Baker City, Oreg.

[73] Assignee: Spatial Dynamics, Ltd., Baker City, Oreg.

[21] Appl. No.: 658,083

[22] Filed: Feb. 20, 1991

[51] Int. Cl.[5] ............................................. G01R 27/04
[52] U.S. Cl. .................................... 324/632; 324/634; 324/636; 324/642; 324/643
[58] Field of Search ............... 324/632, 634, 636, 642, 324/643

[56] References Cited

U.S. PATENT DOCUMENTS

| | | | |
|---|---|---|---|
| 4,234,844 | 11/1980 | Yukl | 324/632 |
| 4,266,188 | 5/1981 | Thompson | 324/606 |
| 4,318,108 | 3/1982 | Yukl | 324/632 |
| 4,651,085 | 3/1987 | Sakurai | 324/639 |
| 4,912,982 | 4/1990 | Yukl | 73/861.05 |
| 4,947,848 | 8/1990 | Yukl | 324/71.1 |

OTHER PUBLICATIONS

"Complex Dielectric Properties of Macroemulsions in the Microwave Region", Journal of Colloid and Interface Science, Thomas, et al., Oct. 1, 1990.

Primary Examiner—Kenneth A. Wieder
Assistant Examiner—Jose M. Solis
Attorney, Agent, or Firm—Kolisch, Hartwell, Dickinson, McCormack & Heuser

[57] ABSTRACT

Method and apparatus for monitoring the volumetric ratio of two constituents of a fluid mixture, e.g. crude oil and water, flowing through a conduit are described. A non-contacting, bidirectional, microwave transmitting/receiving antenna, coupled with a cavity having a conduit through which the fluid mixture passes, generates a signal indicative of the changing dielectric constant of the fluid mixture. By locating the conduit proximate the aperture of the antenna, and by dimensioning the conduit's depth approximately one-fourth the shorter of the two predetermined wavelengths of microwave energy in the two fluid constituents, a substantially linear response of the fluid mixture to the microwave energy incident thereon is produced. The linear response is indicative of the percentage of oil in the fluid mixture flowing through the conduit.

16 Claims, 2 Drawing Sheets

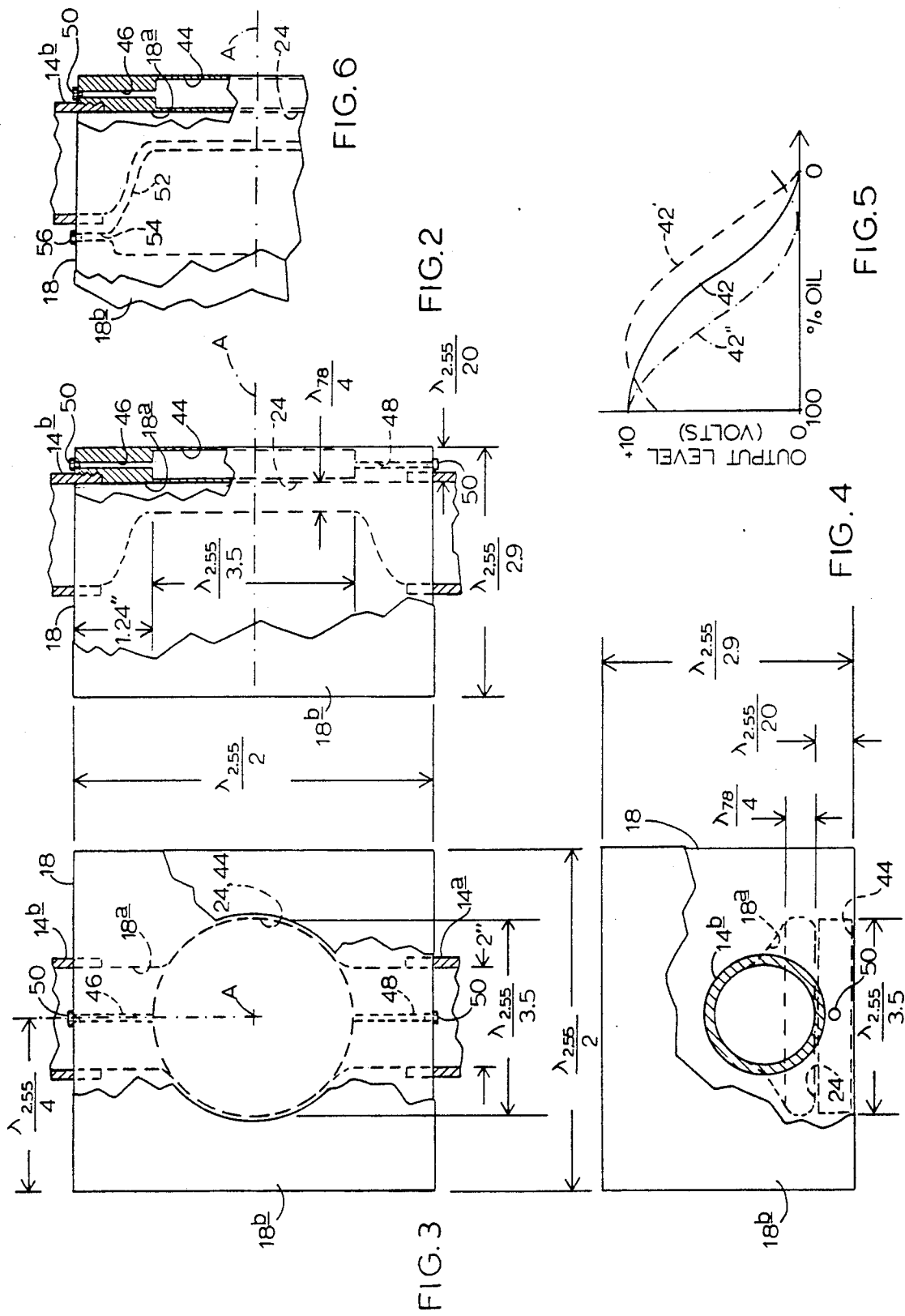

FLUID MIXTURE RATIO MONITORING METHOD AND APPARATUS

BACKGROUND AND SUMMARY OF THE INVENTION

This invention relates generally to fluid (liquid or gas) mixture monitoring method and apparatus. More particularly, it concerns the use of a bidirectional microwave transmitter/receiver to interrogate a conduit through which may be passed a heterogeneous fluid mixture the constituents of which are dielectrically distinct, thereby to determine the ratio of the two fluid mixture constituents within the conduit. The method and apparatus of the invention are described in the context of pumping water to retrieve crude oil from the ground and monitoring at the oil wellhead the volumetric ratio of oil to water in the oil/water fluid mixture flowing thereat. This is a current commercial application with respect to which the invention has particular utility. The invention is also believed to be useful in the protection of the environment and in energy conservation, e.g. by detecting oil pipeline leakage that might contaminate groundwater and waste fossil fuel.

Water is often used to pump crude oil from the ground. On oil-lease land, a landowner earns royalties based roughly upon the oil yielded from the leased land. Heretofore, such royalty calculations have been imprecise, resulting in inaccurate accountings of royalties to landowners. While it has been possible to monitor the mixed oil/fluid volume at each oil wellhead, it has not been possible to monitor the percentage of that volume which is oil, rather than water. Oil and water have different densities and fluid tendencies, but their generally heterogeneous mixture within oil pipelines have made it impossible to perform in-line monitoring of their respective volumes.

As disclosed in my U.S. Pat. No. 4,234,844, issued Nov. 18, 1980, entitled "Electromagnetic Noncontacting Measuring Apparatus", it is possible to monitor electrical conditions by generating and focusing electromagnetic energy at a pair of electrically related, spaced focal points. An important application of such electrical condition monitoring is described in my companion U.S. Pat. No. 4,912,982 issued Apr. 3, 1990, whereby certain fluid parameters such as the rate of flow of a homogeneous fluid through a conduit can be measured. Such flow rate monitoring depends upon the monitoring of the dielectric constant within an interrogation zone, as is described in my companion U.S. Pat. No. 4,947,848, issued Aug. 14, 1990. These patent disclosures are incorporated herein by this reference.

It is a principal object of the invention to provide method and apparatus for monitoring the dielectric constant within an interrogation region embracing a fluid conduit through which passes a heterogeneous mixture of two fluid constituents having disparate dielectric constants to produce a measure of the relative volume of each constituent in the mixture.

Another object is to provide such method and apparatus that can be used to monitor the volumetric ratio, for example, of the constituents of a crude oil/water mixture.

Yet another object is to provide such monitoring compatibly with existing oil wellhead fixtures, and adaptably to future field requirements and standards.

It is still another object to provide such monitoring method and apparatus in real time and with negligent impact on oil wellhead output.

It is also an object to provide high-accuracy monitoring over a wide range of volumetric ratios between constituents.

These and other objects and advantages of the invention will become more fully apparent by reference to the following description and the accompanying drawings.

BRIEF DESCRIPTION OF THE DRAWINGS

FIG. 2 is a detailed side elevation of the cavity portion of the apparatus made in accordance with its preferred embodiment.

FIG. 3 is an end view of the cavity portion corresponding with that of FIG. 2.

FIG. 4 is a top plan view corresponding with the views in FIGS. 2 and 3.

FIG. 5 is a signal waveform illustrating the dimensional parameters that govern the design of the apparatus of the invention.

FIG. 6 is a fragmentary side elevation somewhat like FIG. 2 illustrating modified construction.

DETAILED DESCRIPTION OF THE PREFERRED EMBODIMENT

Figure 1:
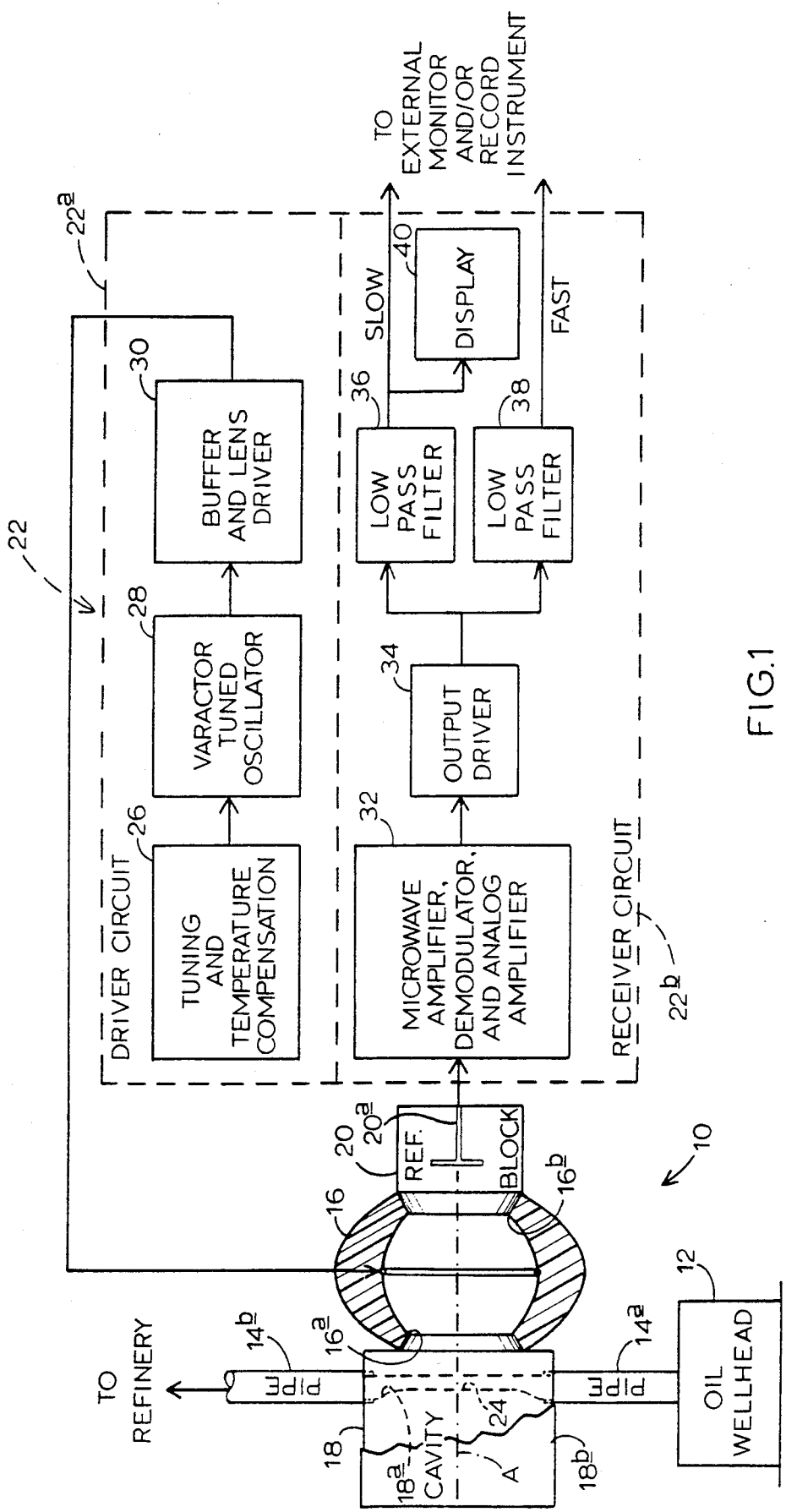
FIG. 1 is a system block diagram illustrating the structure and use of the invention in monitoring the volumetric ratio between crude oil and water in a fluid mixture at the outlet of an oil wellhead.

The apparatus of the invention is indicated in FIG. 1 generally at 10, in connection with an oil wellhead 12 and an oil pipeline 14 including pipeline sections 14a, 14b, which may be made, for example, of polyvinyl chloride, through which passes a fluid mixture of oil and water constituents in a variable volumetric ratio between 0% and 100% of crude oil. Wellhead 12 will be understood to be equipped with pump means for pumping a fluid mixture including water and an oleic fluid such as crude oil from an oil well into means for receiving at least a part of the outflow thereof, or pipeline 14. Apparatus 10 will be seen to provide means coupled with such outflow-receiving means for determining the percentage of such oleic fluid in the fluid mixture outflow from wellhead 12. Thus, the invention may be understood usefully and advantageously to combine oil/water mixture ratio monitoring apparatus with an outlet structure, e.g. oil wellhead 12 and pipeline 14, of an oil well.

Apparatus 10 is shown in block diagram form to include a microwave energy source, or bidirectional transmitter/receiver antenna, or lens, 16 made in accordance with the teachings of the patents referenced herein and having symmetrically opposing apertures 16a, 16b. Operatively coupled with aperture 16a is a cavity 18 and with aperture 16b is a reference block ("REF. BLOCK") 20. Operatively connected with microwave energy source 16 via reference block 20 is driver/receiver means 22 for quantitatively indicating the relative volumes of oil and water constituents in the fluid mixture passing through pipeline 14.

From FIG. 1 cavity 18 may be seen to include a conduit 18a formed therein for passing an oil and water fluid mixture, e.g. by pump means operatively connected with conduit 18a for passing the fluid mixture therethrough, from an inlet connected to pipe section 14a to an outlet connected to pipe 14b. Cavity 18 preferably is made from polystyrene having a dielectric constant K of 2.55, and its entire outer surface, except for the surface that mates aperture 16a of lens 16, is coated with a layer of conductive material 18b, preferably of silver. Reference block 20 preferably is made from a material having a dielectric constant K of approximately 9.0, and is equipped with a receiving element 20a that may be electrically connected to the input of driver/receiver means 22. Conduit 18a may be seen from dashed lines in FIG. 1 to have a complex shape that defines an interrogation region 24 that, in a side elevational view has a smaller dimension than the diameter of pipeline 14. The detailed structure of cavity 18, conduit 18a and interrogation region 24 will be described by reference to FIGS. 2 through 4.

A driver circuit 22a of driver/receiver means 22 includes a tuning and temperature compensation circuit 26 driving a preferably 617-MHz varactor-tuned oscillator 28. The drift-free output of oscillator 28 is buffered and conditioned by a buffer circuit 30 to drive an active element 16c of microwave energy source 16. In response to the signal output by the driver section of driver/receiver means 22, microwave energy source 16 radiates microwave energy at a frequency predetermined by oscillator 28 bidirectionally from apertures 16a, 16b along an axis A. Source 16 is a polarized source, and is oriented and driven in such a way that the electromagnetic plane of polarization lies in the plane of FIG. 1, with the electrostatic plane of polarization intersecting the electromagnetic plane along axis A and extending normal to the plane of FIG. 1. When a fluid mixture passing through conduit 18a consists of two constituents having differentiated dielectric constants K, e.g. crude oil (K≈8.7) and distilled water (K=78), reflected microwave energy along axis A, which is responsive to the fixed radiated energy from source 16 and which is responsive also to the variable dielectric constant of the fluid mixture, is detected by receiving element 20a. Thus, source 16 is capable not only of radiating microwave energy, but also of measuring reflected energy along axis A.

The reflected microwave energy signal output by receiving element 20a is operatively coupled with the input of a receiver section 22b of driver/receiver means 22. The reflected signal is amplified, demodulated and reamplified by circuit 32 to produce an analog output signal ranging from 0-volts (when the oil/water ratio is 0-%) to +10-volts (when the oil/water ratio is 100-%), preferably with better than 1-% midrange accuracy. The demodulated, amplified output thereof is buffered by output driver 34 and routed through a preferably 0-Hz to 0.08-Hz low-pass filter 36 and a preferably 0-Hz to 1.0-kHz low-pass filter 38 to external, respectively low-resolution and high-resolution monitoring and/or recording equipment. The output of low-pass filter 36 is used to drive a display 40, which in real time quantitatively indicates the volumetric ratio between the oil and water constituents of the fluid mixture passing through conduit 18a. Thus, driver 34, filters 36, 38 and display 40 may be thought of as means coupled with microwave energy source 16, and responsive to reflected energy produced by a fluid mixture's influence thereon, for quantitatively indicating the relative volumes of the two constituents of fluid mixture flowing through interrogation region 24.

Those of skill in the arts will appreciate that display 40 may take a variety of forms, including, for example, an analog meter or digital readout calibrated for reading by the user in any desired units, e.g. percentage of oil, percentage of water, etc. In its preferred embodiment, apparatus 10 for use with oil wellhead 12 and pipeline 14 provides for real-time monitoring of the volumetric ratio in a fluid mixture between two constituents, e.g. oil and water, having disparate, and preferably widely separated, dielectric constants.

Turning now collectively to FIGS. 2 through 4, the detailed structure of cavity 18 and conduit 18a formed therein will be described. FIG. 2 is a fragmentary side elevation of cavity 18 and pipeline 14 in their orientation shown in FIG. 1, and shows certain of the important dimensional parameters that enable apparatus 10 repeatably and accurately to operate as described herein. Conduit 18a is dimensioned uniformly along axis A in a region therearound at $\lambda_{78}/4$, where $\lambda_{78}$ is the wavelength of microwave energy at a predetermined frequency as measured in the dielectric constant-dominant fluid constituent, e.g. water (K=78). This dimension corresponds, in the preferred embodiment of the invention in which f=617-MHz, to 0.500-inches. (Persons with skill will appreciate that the dimensions illustrated and described herein are based upon precise operating frequencies and formulae that yield high-precision results, but that of course all given dimensions are subject to manufacturing tolerances.) The proximal wall of conduit 18a is spaced from the proximal face of cavity 18 by $\lambda_{2.55}/20$, where $\lambda_{2.55}$ is the wavelength of the microwave energy, as measured in polystyrene (K=2.55). This dimension corresponds, in the preferred embodiment of the invention, to 0.616-inches. Other dimensions are as illustrated in FIGS. 2 through 4, whether in units of fractional wavelengths or inches, or both.

The preferred dimensions of cavity 18 and the preferred dimensions and shape of conduit 18a are prescribed by various operational requirements of apparatus 10, and are based upon the compatibility thereof with existing pipelines 14 of 2-inches inner diameter. Those skilled in the art will appreciate that the proximal surface of conduit 18a must be substantially closer to aperture 16a, when cavity 18 is coupled as shown in FIG. 1 with lens 16, than either of two predetermined wavelengths at which microwave energy at the predetermined frequency would propagate through the oleic and water constituents, while the propagation velocity of microwave energy over this distance which separates aperture 16a and the proximal surface of conduit 18a is determined by the dielectric constant of the polystyrene material through which the microwave energy propagates. (Nominally, this material is polystyrene, although it will be seen that the material can be other than polystyrene.) For example, the wavelength of microwave energy at f=617-MHz propagating through water $\lambda_{78}$ is 2.167-inches, while the wavelength of microwave energy at the same frequency propagating through polystyrene $\lambda_{2.55}$ is 11.988-inches. Thus, the distance between the proximal edge of conduit 18a and the aperture 16a-mating surface of cavity 18 is expressed as a fraction, preferably one-twentieth, of $\lambda_{2.55}$, the wavelength of microwave energy at the operating frequency through the material, of known dielectric constant, e.g. polystyrene (K=2.55), of which cavity 18 is formed. Similarly, the dimension of conduit 18a along axis A, or the depth of conduit 18a, is expressed as a fraction, preferably one-fourth, of $\lambda_{78}$, the shorter wavelength of the two constituents flowing therethrough, e.g. water.

Referring for a moment to FIG. 3, it may be seen that, in end view, interrogation region 24 within conduit 18a has a generally circular shape concentric with axis A of lens 16 (not shown in FIG. 3, but shown in FIG. 1), and preferably substantially coextensive with the normal to axis defined by aperture 16a of the lens. Thus, conduit 18a may be seen in this view preferably smoothly and continuously to widen in its lateral extent symmetrically between its inlet to which is connected pipe section 14a and its outlet to which is connected pipe section 14b. Conversely, from FIG. 2 conduit 18a may be seen in side view preferably smoothly and continuously to narrow in its distal extent symmetrically between its inlet and its outlet. Ideally, the cross-sectional area of conduit 18a throughout its vertical extent through cavity 18 would remain unchanged, while its cross-sectional shape smoothly changes from generally circular to generally rectangular, whereby the generally right cylindrical interrogation region defining its center, when viewed along axis A, is substantially coextensive, or congruent, with aperture 16a of lens 16.

In the practice of the invention, it has been determined that it is not necessary precisely to maintain the cross-sectional area of conduit 18a, but instead it is believed to be adequate generally to maintain the cross-sectional area and to smoothly contour conduit 18a as shown in FIGS. 2 and 3, thereby to promote the smooth passage of fluid, and to avoid turbulence. The result of any flow constriction within conduit 18a, due to the necessary reshaping thereof in and around interrogation region 24, is a slight pressure gradient, which has been found to have a negligible impact on system throughput.

Referring next to FIG. 5, a waveform representing one-half of a cycle (one-quarter wavelength considering two-way travel) of reflected microwave energy, as measured at receiving element 20a of reference block 20 (shown in FIG. 1), is shown at 42. Waveform 42 is sinusoidal, and its positive peak, or maximum, at an output level of +10-volts corresponds to the proximal plane, or wall, of conduit 18a, and its negative peak, or minimum, at an output level of 0-volts corresponds to a location $\lambda_{78}/4$ away, or at the distal plane, or wall, of conduit 18a. This is the ideal situation, since it permits use of a relatively linear, and relatively high-amplitude, region of the signal waveform responsive to the flow of the fluid mixture through conduit 18a, and thus yields high-sensitivity and high-accuracy measurements of the volumetric ratio of the fluid mixture's constituents.

The dashed line 42′ illustrates an undesirable condition in which the effective distance between conduit 18a and the proximal face of cavity 18, or the plane of aperture 16a, is too small to produce good measurement results. If the interrogation region is slightly misplaced along transmission/reception axis A of lens 16, then the reflected signal intercepted thereby is slightly out of phase and apparatus 10 produces inaccurate, or at least ambiguous, results, for example, in the high-percentage-of-oil range. The dash-dot line 42″ illustrates an equally undesirable condition in which the effective depth of conduit 18a is too great to produce good results. If the interrogation region is slightly oversized depthwise, then the reflected signal intercepted thereby contains more than one-half cycle and apparatus 10 produces inaccurate, or at least ambiguous, results, for example, in the low-percentage-of-oil range.

Referring back briefly to FIGS. 2 through 4, it may be understood now why cavity 18 preferably is equipped with tuning means 44 integral with cavity 18 for tuning apparatus 10. Tuning means 44 preferably takes the form of a thin-walled, sealably fluid mixture-fillable cylindrical chamber interposed conduit 18a and a proximal face of cavity 18. Preferably, chamber 44 is of substantially uniform depth, or dimension along axis A, and is substantially coextensive with interrogation region 24 as viewed along axis A (and, consequently, is substantially coextensive with conduit 18a when viewed along axis A in a region therearound). Tuning means 44 includes a small diameter, e.g. ⅛-inches OD, charging tube 46 through which the chamber can be charged with a medium of known dielectric constant, e.g. a fluid or fluid mixture, and a small diameter bleeding tube 48 through which the charging medium can be discharged. Charging and bleeding tubes 46, 48, preferably define a plane that is parallel with a plane defined by conduit 18a and are of small dimension, thereby having no measurable impact on the dielectric properties of cavity 18. Each of tubes 46, 48 is closeable with a suitable stop or plug 50.

Importantly, fillable chamber 44 is bound in its proximal and distal planes by very thin walls 44a, 44b of the polystyrene material from which cavity 18 is formed, which thin walls are dimensioned to be of negligible volume relative to the volume of chamber 44 and thus have no measurable impact on the dielectric constant of a cylindrical region of diameter $\lambda_{2.55}/3.5$ extending through cavity 18 along axis A from aperture 16a of adjacent lens 16.

The purpose of chamber 44 is to permit the tuning of apparatus 10 by adjustment of the dielectric constant of the cylindrical space between aperture 16a of lens 16 and conduit 18a, the result of which adjustment is effectively to change the electrical distance therebetween. For example, if chamber 44 is filled with water, which has a dielectric constant K of 78, then conduit 18a appears significantly farther from the aperture of the lens than it would if chamber 44 were omitted (effectively filling it with polystyrene the dielectric constant K of which is 2.55) or vacuumed. Chamber 44 can be filled instead with a fluid mixture of homogeneous fluid constituents having disparate dielectric constants, e.g. water (K=78) and glycerin (K≈30), in a volumetric ratio that will produce a filler fluid for chamber 44 having a dielectric constant that will produce the desired change in the effective electrical distance between the proximal plane of conduit 18a and aperture 16a. Such calculations would be performed in accordance with known dielectric constant averaging techniques. By examining the reflected waveform produced by apparatus 10 structured and dimensioned in accordance with the teachings herein, and by introducing an appropriate fluid mixture into chamber 44 via charging tube 46 and bleeding tube 48, it is possible to obtain the proper phase of the reflected signal relative to the location of the proximal plane, or wall, of conduit 18a. Thus, tuning means 44 cooperates with lens 16 and cavity 18 to provide a desired-characteristic, reflected-energy response to radiated energy in driver/receiver means 22. Proper tuning provides a maximum response when the system is 100-% filled with the lower dielectric constant material, and the minimum response when the system is 100-% filled with the higher dielectric constant material.

One should note at this point that what might be thought of as the long, or fluid flow, axes of conduit 18a and region 24, and of chamber 44 and tubes 46, 48, extend substantially normal to what was previously described as the electrostatic plane of polarization of source 16. This orientation improves accuracy of performance by making the feeder and discharge ends of region 24 and chamber 44 substantially invisible.

FIG. 6 herein illustrates a modified construction in which, to the left in this figure of conduit 18a and interrogation region 24, there is formed a chamber 52 which may be viewed as a chamber of revolution symmetric with respect to axis A. Communicating with this chamber are a charging tube 54, which is like previously mentioned charging tube 46, and a bleeder tube (not shown) which is similar to previously mentioned bleeder tube 48. Plugs, such as plug 56, close the outer ends of the charging and bleeder tubes.

This modified structure is also usable as a tuning means fillable with a medium of a desired dielectric constant and usable to change the apparent electrical distance of the distal wall of interrogation region 24 relative to the lens aperture. The specific modification shown in FIG. 6 thus employs tuning means on opposite axial sides of the region of interrogation.

Yet another modification which might be useful in certain instances is one wherein a tuning means like 44 is completely omitted, the conduit structure is shifted very closely adjacent the lens aperture, and a "rear" tuning means, such as 52, is employed alone.

Those skilled in the arts will appreciate that the operating frequency need not be 617-MHz, but may be any appropriate frequency, with corresponding changes to other dimensional and operational parameters of apparatus. The skilled will also appreciate that slight changes in the operating frequency effectively will make conduit 18a appear slightly closer to or farther from aperture 16a, although such will also desensitize, and thus reduce the signal-to-noise ratio, of transmitter/receiver antenna 16. Those of skill also will appreciate that fluid constituents other than oil and water may be passed through conduit 18a and their volumetric ratio per unit time therein determined. For example, other liquid mixtures, as well as gas mixtures, may be monitored. Persons skilled in the arts will appreciate that conventional temperature compensation techniques may be used to ensure the long-term stability and accuracy, especially in extreme oil wellhead environments, of driver/receiver means 22 of apparatus 10.

The preferred method of the invention now may be understood from an understanding of the preferred embodiment described above. As may be surmised, the method achieves monitoring of the volumetric ratio of two dielectrically disparate fluid constituents, or fluid constituents having measurably different dielectric constants. Preferably, the method involves a first step of producing a flow, e.g. by pump means, of a fluid mixture of two dielectrically different constituents, e.g. oil and water, through a defined interrogation region such as interrogation region 24. As illustrated in FIGS. 2 and 4, interrogation region 24 bounded proximally and distally by conduit 18a preferably has a dimension along axis A that is substantially less than the predetermined wavelength at f=617-MHz of microwave energy from lens 16 propagating through the higher dielectric constant constituent, e.g. water (K=78). A second step involves directing, or projecting, microwave energy from a microwave source, e.g. lens 16, along axis A. A third step involves generating an output, e.g. the SLOW or FAST output signal from driver 34 and filter 36 or 38 or display 40, indicative of the instantaneous volumetric ratio, or the volumetric ratio per unit time, between the two constituents within the interrogation region. The third step preferably is performed by measuring, e.g. via receiving element 20a and amplifier/demodulator 32, reflected energy responsive, as illustrated in FIG. 5, to the fluid mixture's passing, or flow, through the interrogation region. Preferably, the flow-producing step is performed by passing the water and oleic fluid mixture through the interrogation region within a conduit, e.g. conduit 18a.

A further step of locating conduit 18a relative to the source in such a manner that the predetermined distance therebetween is substantially less than either of the predetermined wavelengths of the fluid mixture's constituents ensures that, as illustrated in FIG. 5, the reflected energy measured by amplifier/demodulator 32 is not only repeatably, but also unambiguously, representative of the relative constituent volume ratio. Optionally, and in order to permit long-term, real-time monitoring of the volumetric ratio between the oil and water constituents of the fluid mixture, the passing and projecting steps are repeated for a predetermined period of time over which monitoring is desired. In this way, the volumetric ratio of the constituents passing through the conduit, and thus through pipeline 14 (refer to FIG. 1), during the prescribed period of time is determined.

Clearly, if the flow rate of water and oleic fluid mixture is known, or if the total mixture volume during such period of time is known, then the oil yield from the well during such period of time can be calculated. Yet the method and apparatus of the invention by which oil, for example, as a percent of total fluid flowing in a conduit is monitored are non-invasive. Moreover, they are compatible with known oil wellhead and pipeline configurations, so that existing installations readily may be upgraded with the monitoring capability. Those of skill in the art will appreciate that the apparatus and method of the invention are useful for the monitoring of any two dielectrically disparate fluid mixture constituents, e.g. the volumetric ratio of kerosene in a kerosene/water fluid mixture can be determined. Very different (non-oleic and non-hydrous) constituent volume contributions to a fluid mixture also can be monitored, by straightforwardly changing, for example, the physical parameters of the conduit and its proximity to the lens' aperture.

Those skilled in the arts also will appreciate that other materials may be used in the structure of the cavity, for example, yet it still will be possible to generate a signal indicative of the relative contributions to the whole of the fluid mixture within the interrogation region of each fluid constituent. The orientation of the apparatus of the invention may be changed without adversely impacting its ability to generate useful ratiometric results. For example, the apparatus shown in FIG. may be turned 90° so that gravity assists in an effective separation of fluid constituents having different densities, thereby to avoid any polarizing effects of an oil/water fluid mixture on the accuracy of the ratiometering. For purposes of fine tuning apparatus 10, or in order to render a more general purpose fluid constituent ratio monitor, the dielectric constant of the material within a thin-walled chamber between the lens' aperture and the interrogation region of the conduit may be adjusted, e.g. by introducing a fluid mixture of known dielectric constant higher than that of polystyrene, but less than that of water, by means described and illustrated herein, thereby to effect optimal performance for a given operating frequency, cavity and conduit design, and fluid mixture.

Accordingly, while a preferred method for practicing the invention, and a preferred embodiment of the apparatus of the invention, have been described herein, it is appreciated that virtually unlimited modifications are possible that come within the scope of the invention.

It is claimed and desired to secure by Letters Patent:

1. For monitoring the volumetric ratio in a fluid mixture between two constituents having differentiable dielectric constants, apparatus comprising:
   a microwave energy source capable of radiating microwave energy at a predetermined frequency along a given axis, said source further being capable of measuring reflected energy along said given axis which is responsive to said radiated energy;
   means proximate said source defining a conduit through which a fluid mixture to be monitored can pass; and
   tuning means for adjusting effective electrical distances for radiation propagating along said axis, said tuning means including at least one chamber positioned along said axis and adjacent one side of said conduit, said chamber being sealably fillable with a medium having a known dielectric constant.

2. The apparatus of claim 1 wherein said turning means takes the form of a chamber on the side of said conduit which faces toward said source.

3. A method of monitoring the volumetric ratio of two dielectrically disparate fluid constituents comprising:
   passing a fluid mixture of two dielectrically distinct constituents through a conduit formed within a cavity having a known dielectric constant, such conduit being dimensioned along a given axis at substantially less than the propagation wavelength of microwave energy at a given frequency through the one of such constituents having the higher dielectric constant, such conduit being of substantially uniform dimension along the given axis in a region therearound and such conduit being of generally rectangular cross section in a region therearound when viewed normal to the given axis;
   directing microwave energy along such given axis into such conduit from a source operatively coupled with such cavity at a predetermined distance from such conduit, with such source operating at such given frequency, such predetermined distance being substantially less than the propagation wavelength of microwave energy at such given frequency through either one of such constituents; and
   by measuring reflected energy responsive to said passing of such fluid mixture through such conduit and to said directing of such microwave energy, generating an output indicative of the volumetric ratio between such constituents.

4. The method of claim 3, wherein said passing is of water and oleic constituents.

5. The apparatus of claim 1 wherein said tuning means cakes the form of a chamber disposed on the side of said conduit which faces away from said source.

6. A method of monitoring the volumetric ratio between two dielectrically disparate fluid constituents comprising:
   passing a fluid mixture of two constituents having measurably different dielectric constants through a conduit;
   projecting microwave energy of a predetermined frequency along a given axis from a microwave source at a predetermined distance from and into such conduit and measuring reflected energy responsive thereto, wherein such reflected energy is dependent upon the instantaneous volumetric ratio between such two constituents of such fluid mixture within a defined interrogation region within the conduit;
   tuning such microwave source relative to such conduit to provide a desired-characteristic reflected-energy response to such projected energy, said tuning including introducing a fluid mixture having a known dielectric constant into a chamber interposed such conduit and such source, thereby producing a desired change in the effective electrical distance therebetween; and
   repeating said passing and said projecting-measuring steps for a predetermined period of time to determine the volumetric ratio of such two constituents of such fluid mixture passing through such conduit during such period of time.

7. The method of claim 6, wherein such predetermined distance between the source and an outer surface of the conduit proximal to the source is substantially less than the predetermined wavelength of microwave energy at the given frequency in either of such two constituents.

8. For monitoring the volumetric ratio in a fluid mixture between two constituents having differentiable dielectric constants, apparatus comprising:
   a transmitter/receiver lens capable of radiating microwave energy at a predetermined frequency along a given axis, said lens further being capable of measuring reflected energy along said axis which is responsive to said radiated energy, said lens having an aperture from which said microwave energy is radiated;
   a cavity coupled with said lens, said cavity including a conduit through which a fluid mixture can pass, said conduit being located near a face of said cavity that is proximate said aperture, said conduit being of substantially uniform dimension along said given axis in a region therearound that is substantially coextensive with said aperture, said dimension being substantially less than the shorter of two predetermined wavelengths at which microwave energy at said predetermined frequency would propagate through such constituents;
   means operatively connected with said conduit for passing such a fluid mixture through said conduit; and
   means coupled with said lens and responsive to said reflected energy for quantitatively indicating the relative volumes of such constituents in said passing fluid mixture.

9. The apparatus of claim 8, wherein said transmitter/receiver lens includes an antenna having an aperture of a defined area substantially normal to said given axis and wherein said conduit when viewed along said given axis is substantially coextensive with said defined area.

10. The apparatus of claim 8, wherein said conduit is located at a distance from said source that is substantially less than either of two predetermined wavelengths at which microwave energy at said predetermined frequency would propagate through such constituents.

11. The apparatus of claim 10, wherein said cavity is of a material having a known dielectric constant, wherein said distance is approximately one-twentieth of the predetermined wavelength at which microwave energy at said predetermined frequency would propagate through said material.

12. The apparatus of claim 8, wherein said dimension is approximately one-quarter of said shorter of said two predetermined wavelengths.

13. For monitoring the volumetric ratio in a fluid mixture between two constituents having differentiable dielectric constants, apparatus comprising:
a microwave energy source capable of radiating microwave energy at a predetermined frequency along a given axis, said source further being capable of measuring reflected energy along said given axis which is responsive to said radiated energy;
a cavity coupled with said microwave energy source, said cavity including a conduit through which a fluid mixture can pass, said conduit being located near a face of said cavity that is proximate said source, said conduit being of substantially uniform dimension along said given axis in a region therearound, said dimension being substantially less than the shorter of two predetermined wavelengths at which microwave energy at said predetermined frequency would propagate through such constituents;
tuning means integral with said cavity for adjusting the effective electrical distance between said conduit and said source, thereby to provide a desired-characteristic reflected-energy response to said radiated energy, said tuning means including a chamber interposed said conduit and said face of said cavity, said chamber being sealably fillable with a medium having a known dielectric constant;
means operatively connected with said conduit for passing such a fluid mixture through said conduit; and
means coupled with said source and responsive to said reflected energy for quantitatively indicating the relative volumes of such constituents in said passing fluid mixture.

14. The apparatus of claim 13, wherein said turning means takes the form of a thin-walled chamber interposed said face of said cavity and said conduit, said chamber being sealably fillable with a medium having a known dielectric constant.

15. The apparatus of claim 14, wherein said chamber is of substantially uniform dimension along said given axis and is substantially coextensive with said conduit when viewed along said given axis in a region therearound.

16. The apparatus of claim 1 wherein said tuning means takes the form of a pair of chambers disposed on opposite sides of said conduit relative to said source.

* * * * *